United States Patent [19]

Sjöqvist

[11] Patent Number: 5,068,923
[45] Date of Patent: Dec. 3, 1991

[54] NOISE ATTENUATOR ATTACHMENT ARM

[75] Inventor: Ingvar Sjöqvist, Linneavägen, Sweden

[73] Assignee: Milmas AB, Gothenburg, Sweden

[21] Appl. No.: 598,713

[22] PCT Filed: Apr. 27, 1989

[86] PCT No.: PCT/SE89/00238

§ 371 Date: Oct. 24, 1990

§ 102(e) Date: Oct. 24, 1990

[87] PCT Pub. No.: WO89/10107

PCT Pub. Date: Nov. 2, 1989

[30] Foreign Application Priority Data

Apr. 28, 1988 [SE] Sweden ............... 8801602-7

[51] Int. Cl.⁵ .............. A42B 1/06; G10K 11/00
[52] U.S. Cl. ............................ 2/209; 2/423; 181/129; 381/188
[58] Field of Search ........... 2/209, 208, 417, 423, 2/418, 419; 128/864, 866; 381/72, 183, 187, 188, 205, 25; 379/430, 431; 181/129, 175, 207, 209

[56] References Cited

U.S. PATENT DOCUMENTS

| | | | |
|---|---|---|---|
| 1,225,422 | 5/1917 | Feher | 2/209 |
| 2,782,423 | 2/1957 | Simon et al. | 2/209 |
| 3,085,253 | 4/1963 | Ulrich et al. | 2/209 |
| 3,430,261 | 3/1969 | Benner | 2/209 |
| 3,505,684 | 4/1970 | Hutchinson et al. | 2/209 |
| 3,845,505 | 11/1974 | Davison et al. | 2/423 |
| 3,864,756 | 2/1975 | Desimone | 2/209 |
| 4,347,631 | 9/1982 | Newcomb | 2/209 |
| 4,615,050 | 10/1986 | Lönnstedt | 2/209 |
| 4,727,585 | 2/1988 | Flygstad | 2/209 |
| 4,944,361 | 7/1990 | Lindgren et al. | 2/423 |

FOREIGN PATENT DOCUMENTS

| | | | |
|---|---|---|---|
| 452623 | 5/1913 | France | 2/209 |
| 910149 | 3/1982 | U.S.S.R. | 2/209 |

Primary Examiner—Werner H. Schroeder
Assistant Examiner—Amy Brooke Vanatta
Attorney, Agent, or Firm—Sughrue, Mion, Zinn, Macpeak and Seas

[57] ABSTRACT

A sprung attachment arm for sound attenuating devices intended to form part of a head stirrup or to be fitted to a protective helmet. The arm (2) is constructed so that one end thereof can be attached to a protective ear muff (4) in a manner to spring-press the ear muff against the head of the wearer. The arm (2) has a substantially straplike configuration along at least part of its length and a cross-section through the straplike part presents at least one part which functions as a sprung leg (5) which forms an angle with adjacent parts of the straplike part (2). The straplike part (2) will preferably include at least two mutually angled sprung legs (5). A sprung arm of this configuration will produce an abutment pressure which will vary only slightly in response to different head sizes.

10 Claims, 1 Drawing Sheet

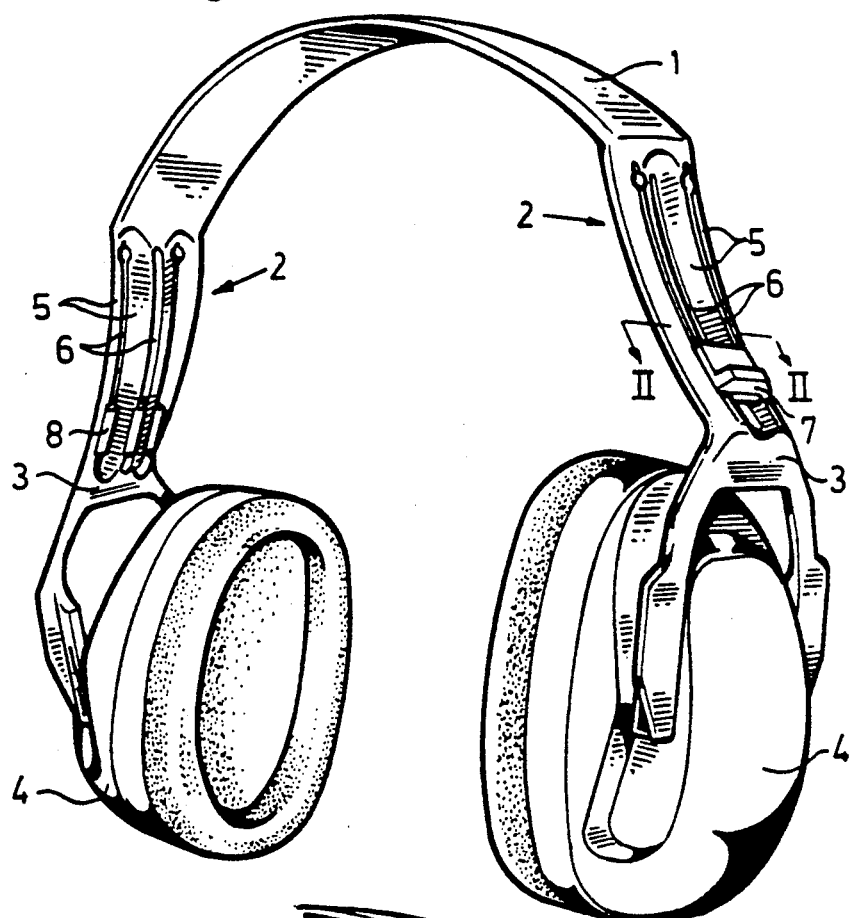
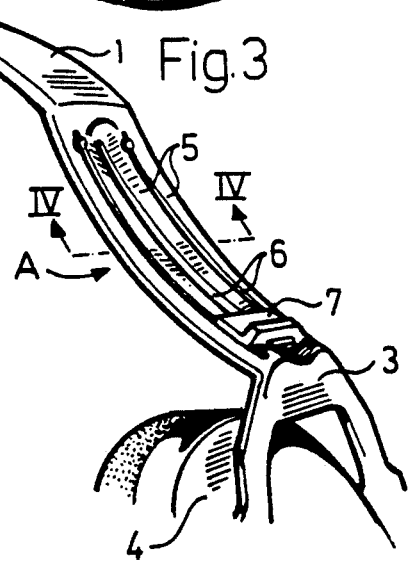
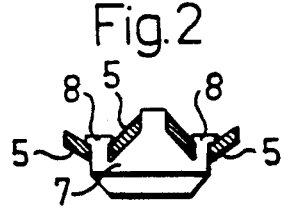
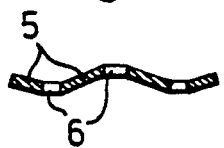
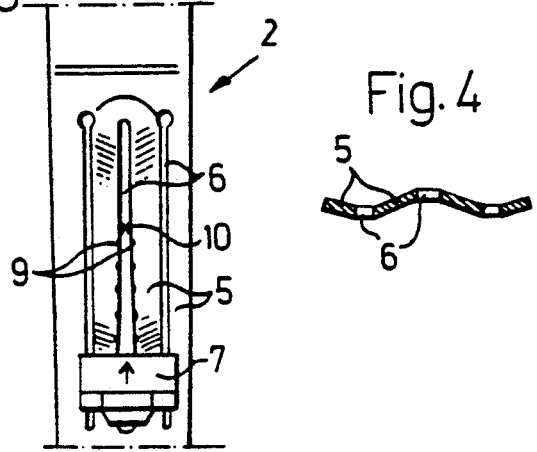

NOISE ATTENUATOR ATTACHMENT ARM

BACKGROUND OF THE INVENTION

The present invention relates to an attachment arm for a noise attenuating device which is intended to form part of a head stirrup or head strap or to be fitted to a protective helmet, and one end of which arm can be connected to a noise attenuating, protective ear muff, such as to enable the muff to be spring-pressed against the head of the wearer.

People who occupy excessively noisy environments are obliged to wear some form of noise attenuating device to protect the wearer against noise injury. These devices are normally fitted to a protective helmet, such as those worn in forestry work, by miners, on building sites, in dockyards, and like places. The noise attenuating devices are connected to the shell of the helmet by means of spring-biased arms. The need for such noise attenuating devices, however, is also found in other connections, where the need for a protective helmet is not found. In this case, the noise attenuating device is carried by a so-called head stirrup or strap.

Two main requirements of a satisfactory noise attenuating device are that the device will attenuate noise effectively and efficiently and that it is comfortable to wear. However, since these two requirements are essentially opposed to one another, they are difficult to realize in practice. In order to obtain good protection against intense noise, it is necessary for the noise attenuating device to be pressed hard against the wearer's head, so as to prevent the occurrence of noise leakage passages between the attenuator muff sealing ring and the wearer's head. A relatively tight abutment pressure is required in the case of head stirrups, in order to ensure that the stirrup will be held firmly on the head of the wearer. This abutment pressure, however, must not be so excessive as to render the sound attenuating device uncomfortable when worn. Thus, from the aspect of comfort, the abutment pressure should be as light as possible. This may lead, however, to poor sound attenuation and poor retention of the stirrup on the head of the wearer.

Tests have shown that if the person who occupies an environment of intense noise while wearing a noise attenuating device is obliged to remove the device for 10% of the total occupation time, the risk of injury through noise is essentially no less than if the person wore no protection at all.

The protective effect of the device will be greatly impaired, even when the device is removed for 3% of the total occupation time, while an unprotected span of as little as 1% of said total time will result in a marked decrease in the protective effect. It is possible to conclude from this that the endeavor to achieve the tightest possible abutment pressure, and thus the maximum sound attenuating effect, is counter-productive if it results in the need to remove the device at times, for the sake of comfort.

Those noise attenuating devices earlier available on the market are constructed to afford good noise attenuation and, in the case of head stirrups, also good retention with head sizes above a certain minimum size, and also good comfort, although the retention of such head stirrups is less positive when the head size is below a given maximum size. In the case of large head sizes, the noise attenuating device will often press hard against the wearer's head, resulting in a reduction in comfort, whereas in the case of small head sizes the abutment pressure is so light as to impair the noise attenuating effect of the device and to render the head stirrup less secure. The difference in abutment pressures can differ to a significant extent between small and large head sizes.

These problems are amplified when attempting to manufacture the head stirrups from a plastics material, since the abutment pressure engendered with such stirrups will decrease over the time in which the stirrup is in use and will be restored to its original value when the stirrup is allowed to relax for a given length of time. Consequently, the abutment pressure needs to be very high at the beginning of a working shift in order for sufficient holding force to remain at the end of the shift and to provide for effective noise attenuation for the duration of said shift, all to the detriment of comfort.

SUMMARY OF THE INVENTION

The object of the present invention is to provide a sprung noise-attenuator attachment arm with which the aforesaid abutment pressure will only vary slightly with different head sizes. One embodiment of the invention will enable the abutment pressure to be adjusted. In accordance with the invention, an attachment arm of the aforesaid kind is characterized in that the arm is substantially of straplike configuration along at least a part of its length; and in that a cross-section through said straplike part presents at least one part which functions as a sprung leg which forms an angle with adjacent parts of the straplike part.

A sprung leg of this construction will exert a relatively constant abutment pressure over a given range, since the leg angle relative to said adjacent parts will increase as the arm is bent outwards, which means that the leg will become less rigid at the same time as further outward bending of the arm will result in an increase in spring force. These phenomena thus counteract one another and result in a relatively constant spring characteristic.

In order to ensure that the arm will move in a straight line as the arm is bent outwards, the straplike part of the arm will preferably include at least two mutually angled sprung legs, preferably two pairs of V-angled legs.

The side edges of each sprung leg can be separated from adjacent parts of the straplike part and from adjacent legs, by means of longitudinally extending slots. Alternatively, the slots may be replaced with weakened areas in the material from which the arm is made.

In order to enable adjustments to be made to the abutment pressure, e.g. so that compensation can be made for the reduction in abutment pressure that occurs in time in the case of plastic head stirrups, the stirrup structure will preferably include elements which can be attached to the straplike parts and which are operative in counter-acting the tendency of the angled legs to rotate as the arms are bent outwards. These elements will suitably be displaceable along the angled legs.

In those instances when the sprung legs are separated by means of slots, said elements will preferably have the form of slides provided with bars which fit into the slots. The slots may therewith narrow from the ends thereof nearest the ear muffs along at least half of the length of the slot, such that said bars will urge the angled legs progressively apart as the slides are moved in the direction of the slot taper, therewith to increase the abutment pressure still further.

BRIEF DESCRIPTION OF THE DRAWINGS

The invention will now be described in more detail with reference to the accompanying drawing.

FIG. 1 illustrates a head stirrup provided with arms according to the invention for the attachment of protective ear muffs.

FIG. 2 is a section taken on the line II—II in FIG. 1.

FIG. 3 illustrates outward bending of one arm of the stirrup shown in FIG. 1.

FIG. 4 is a section taken on the line IV—IV in FIG. 3.

FIG. 5 is a straight-on side view of one attachment arm of the stirrup shown in FIG. 1.

DETAILED DESCRIPTION OF THE PREFERRED EMBODIMENT

The head stirrup illustrated in FIG. 1 includes an upper, connecting part 1 which is intended to lie on the crown of the head and which connects the two sprung attachment arms 2, one to the other. Each end of respective arms 2 distal from the connecting, crown part 1 merges with a bifurcate holder 3, the legs of which are hingedly and displaceably attached to an associated protective ear muff 4. The whole of the head stirrup is preferably made as a one piece structure from a springy plastics material having good spring restoring properties, for instance glass-fibre reinforced nylon or an acetal plastic material.

In the case of the illustrated embodiment, each attachment arm 2 is configured to provide four elongated sprung legs 5, each of which forms an angle with the leg immediately adjacent thereto. The legs are separated mutually by slots 6 and are V-angled in pairs relative to one another, see FIG. 2.

In the starting position shown in FIG. 2, respective legs 5 form a relatively large angle with a horizontal plane through the arm, which means that the sprung legs will be relatively rigid in this position. Consequently, even if the wearer's head is relatively small and requires only slight outward bending of the arms, there is obtained a relatively large abutment force sufficient to press the ear muffs against the head of the wearer such as to achieve fully satisfactory noise attenuation or damping.

When the stirrup is to be fitted to a larger head size, the arms 2 must be bent outwards to a greater extent than in the case of small head sizes, as indicated by the arrow A in FIG. 3. As will be seen from FIG. 4, increased outward bending of the arm will result in a marked decrease in the angle formed by the legs 5 with said horizontal plane through respective arms 2 and when the arms are bent outwards to a very considerable extent, said angle will be parallel with said horizontal plane. This rotation causes the rigidity of the legs to decrease as the arms are bent outwards, thus counteracting the increase in spring force which results from said outward bending of the arms. The abutment pressure of the ear muffs 4 against the head is thus relatively independent of the size of the wearer's head. In respect of head sizes which vary from 130 to 170 mm, measured between the orifices of the auditory canals, the abutment pressure can be maintained within the range of 9–11N, which will afford good sound attenuation combined with good comfort. This interval of 2N shall be compared with conventional head stirrups, with which the variation in abutment pressure can be as high as 6–8N.

The number of sprung legs, and therewith the number of slots, may be varied as desired. However, there will preferably be at least two legs or a multiple of two, such as to obtain pairwise opposing legs which will cause the ear muffs 4 to move linearly away from one another when the arms 2 are moved outwards. As an alternative to slots 6, the outer marginal edges of the legs 5 may be mutually joined by weakened material portions which will function as hinges. Angled legs can also be combined with planar legs.

In the case of the illustrated embodiment, the rigidity of the sprung arms 2 can be adjusted with the aid of slides 7, which are provided with bars 8 which enter the slots 6 so as to enable the slides to be displaced along said slots, see FIG. 2. The centre part of each slide 7 is configured to correspond to the angle between the centrally located legs 5 and consequently said slides 7 will prevent this angle from changing when the arms 2 are bent outwardly. The rigidity of the legs 5 can thus be adjusted, by sliding the slides 7 along said legs.

As shown in FIG. 5, at least the centre slot 6 will preferably have a narrowing width, such that when a slide 7 is displaced along the slot in the direction of the slot taper, the bar 8 extending into the slot will urge the adjacent legs progressively further apart and therewith further increase the spring force. In this regard, the slot may be provided with setting notches 9 which will allow the slide to be moved between distinct positions. As shown in FIG. 5, the slot may also be provided with stop means 10, since there is often no reason to displace the slide 7 further than essentially midway along the slot.

The ability to adjust the pressure at which the protective ears muffs abut the wearer's head, in the aforedescribed simple manner, affords significant advantages, since it enables the abutment pressure to be adapted as desired to the level of noise prevailing in the noise intense environment occupied by the wearer. As before mentioned, plastic head stirrups tend to fatigue during a working shift, in which case the abutment pressure can be adjusted with the aid of the slides 7.

The invention has been described in the aforegoing with reference to a head stirrup which is made in one piece. It will be understood, however, that the stirrup may be assembled from separate parts and that the arms may be made separately. The arms can then be joined to the connecting piece 1 in some suitable manner and may alternatively be connected to and carried by a protective helmet.

The illustrative embodiments may also be modified in various ways within the concept of the invention. For instance, the slide 7 may be exchanged for some other form of element capable of controlling flattening of the sprung legs as the attachment arms 2 are bent or flexed outwardly.

I claim:

1. A sprung attachment arm for a sound attenuating device forming part of a head stirrup or adapted to be fitted to a protective helmet, said arm (2) being adapted at one end thereof for attachment to a protective ear muff (4), wherein the arm has an elongate, straplike configuration along at least part of a length thereof, and defines at least one element which functions as a sprung leg (5), and which forms an angle with adjacent elements of the straplike part, said angle increasing as the arm is bent outwardly such that the muff is spring-biased against the head of a wearer with a relatively constant pressure over a relatively wide bending range.

2. An arm according to claim 1, wherein the straplike part includes at least two mutually angled sprung legs (5).

3. An arm according to claim 2, wherein the straplike part includes two pairs of V-angled sprung legs (5).

4. An arm according to claim 3, wherein side edges of each angled sprung leg (5) are spaced from adjacent elements of the straplike part and from adjacent angled legs by longitudinally extending slots (6).

5. An arm according to claims 1, 2 or 3, wherein side edges of each angled sprung leg (5) are joined to adjacent elements of the straplike part and to adjacent angled sprung legs via weakened material portions.

6. An arm according to claim 4, further including an element which can be attached to the straplike part of said arm for counteracting the rotation of the angled sprung legs (5) that occurs when said arm is bent outwardly, therewith enabling the abutment pressure on the wearer's head to be adjusted.

7. An arm according to claim 6, wherein said element (7) can be displaced along the angled sprung legs (5).

8. An arm according to claims 6 or 7, wherein said element has the form of a slide provided with bars (8) which project into said slot (6).

9. An arm according to claim 8, wherein said slots (6) narrow from ends thereof located adjacent the ear muff (4) along at least half the length of said slots; and said bars are adapted to urge the sprung legs (5) progressively further apart as said slide (7) is moved along the slots in their direction of taper.

10. An arm according to claim 8, wherein the sprung legs (5) include means (9) for positional adjustment of the displaceable element (7).

* * * * *